(12) United States Patent
Aeby et al.

(10) Patent No.: US 11,298,304 B2
(45) Date of Patent: Apr. 12, 2022

(54) TWO COMPONENT HAIR TREATMENT KIT COMPRISING A HAIR COLORING CREAM AND A DEVELOPER COMPOSITION COMPRISING A SPECIFIC TENSIOACTIVE COMPOUND

(71) Applicant: Laboratoire Biosthétique Kosmetik GmbH & Co. KG, Pforzheim (DE)

(72) Inventors: Johann Aeby, Marly (CH); Otto Richard Göttel, Marly (CH)

(73) Assignee: Laboratoire Biosthétique Kosmetik GmbH & Co. KG, Pforzheim (DE)

( * ) Notice: Subject to any disclaimer, the term of this patent is extended or adjusted under 35 U.S.C. 154(b) by 0 days.

(21) Appl. No.: 17/041,697

(22) PCT Filed: Mar. 27, 2018

(86) PCT No.: PCT/EP2018/057811
§ 371 (c)(1),
(2) Date: Sep. 25, 2020

(87) PCT Pub. No.: WO2019/185127
PCT Pub. Date: Oct. 3, 2019

(65) Prior Publication Data
US 2021/0128427 A1 May 6, 2021

(51) Int. Cl.
*A61Q 5/10* (2006.01)
*A61K 8/22* (2006.01)
(Continued)

(52) U.S. Cl.
CPC .................. *A61K 8/22* (2013.01); *A61K 8/06* (2013.01); *A61K 8/342* (2013.01); *A61K 8/416* (2013.01);
(Continued)

(58) Field of Classification Search
CPC ... A61Q 5/10; A61K 8/22; A61K 8/41; A61K 2800/4324; A61K 2800/88;
(Continued)

(56) References Cited

U.S. PATENT DOCUMENTS 5,480,459 A 1/1996 Mager et al.
5,609,651 A 3/1997 Mager et al.
(Continued)

FOREIGN PATENT DOCUMENTS

EP 0650718 A1 5/1995
EP 0594811 B1 6/1996
(Continued)

OTHER PUBLICATIONS

International Search Report; European Patent Office; International Application No. PCT/EP2018/057811; dated Oct. 24, 2018; 3 pages.
(Continued)

*Primary Examiner* — Eisa B Elhilo
(74) *Attorney, Agent, or Firm* — Taft Stettinius & Hollister LLP

(57) ABSTRACT

The present invention relates to a kit, preferably for coloring keratin fibers, the kit comprising in spatially separated form at least two kit components: A) a first kit component comprising at least these constituents: at least one alkaline agent; at least one amino acid; at least one organic phosphate ester compound selected from the group consisting of a monoester of a phosphate of one or more alkoxylated fatty alcohols, a diester of a phosphate of one or more non-alkoxylated fatty alcohols, and a mixture of both; water; and optionally at least an oxidative dye; water; and B) a second kit component comprising at least these constituents: at least one emulsifier; hydrogen peroxide; at least one fatty alcohol; and water. The invention relates also to a process of manu-
(Continued)

facturing a composition which is the second kit component, a composition obtainable by such process, a ready-to-use composition, a way of preparing such and to a use of an emulsifier as in formula (I) and defined above in combination with the organic phosphate ester compound defined above to reduce the viscosity of haircoloring creams.

23 Claims, 4 Drawing Sheets

(51) Int. Cl.
*A61K 8/06* (2006.01)
*A61K 8/34* (2006.01)
*A61K 8/41* (2006.01)
*A61K 8/44* (2006.01)
*A61K 8/55* (2006.01)

(52) U.S. Cl.
CPC ............... *A61K 8/44* (2013.01); *A61K 8/55* (2013.01); *A61Q 5/10* (2013.01); *A61K 2800/10* (2013.01); *A61K 2800/4324* (2013.01); *A61K 2800/882* (2013.01)

(58) Field of Classification Search
CPC .... A61K 2800/882; A61K 8/44; A61K 8/416; A61K 8/55; A61K 8/604; A61K 8/06; A61K 8/342; A61K 2800/10
USPC .......................................................... 8/405
See application file for complete search history.

(56) References Cited

U.S. PATENT DOCUMENTS

| | | |
|---|---|---|
| 6,610,514 B2 | 8/2003 | Kondo et al. |
| 10,039,701 B2 | 8/2018 | Aeby et al. |
| 2003/0226217 A1 | 12/2003 | Bowes et al. |
| 2006/0117498 A1* | 6/2006 | Bureiko ............... A61K 8/556 8/406 |
| 2012/0288570 A1 | 11/2012 | Zhu et al. |
| 2013/0164361 A1* | 6/2013 | Enan ...................... A01N 65/00 424/405 |
| 2013/0167863 A1 | 7/2013 | Schmelz et al. |
| 2014/0053345 A1* | 2/2014 | Rapold ................... A61K 8/41 8/407 |
| 2015/0082554 A1* | 3/2015 | Allard ..................... A61K 8/31 8/408 |
| 2017/0333306 A1 | 11/2017 | Yamada et al. |

FOREIGN PATENT DOCUMENTS

| | | |
|---|---|---|
| EP | 1669105 A1 | 6/2006 |
| JP | 1997002924 A | 1/1997 |
| JP | 2017522351 A | 8/2017 |
| RU | 2533485 C2 | 11/2014 |
| WO | 2011087786 A1 | 7/2011 |

OTHER PUBLICATIONS

Written Opinion of the International Searching Authority; European Patent Office; International Application No. PCT/EP2018/057811; dated Oct. 24, 2018; 5 pages.
Russian Office Action; Federal Service for Intellectual Property; Russian Application No. 2020129148/04(052140); dated Dec. 9, 2021; 7 pages.
Belikov; Pharmaceutical chemistry; Moscow: "High School", 1993; 8 pages.
Sutyagin et al.; Chemistry and Physics of Polymers Tutorial; Ministry of Education of the Russian Federation Tomsk Polytechnic University; 7 pages.
Japanese Office Action; Japan Patent Office; Japanese Application No. 2021-501079; dated Jan. 6, 2022; 5 pages.
Permanent Hair Cream Colourant, ID 3699647, Mintel GNPD, Jan. 2016, URL https://www.portal.mintel.com.
One Push Hair Colour, ID 2882155, Mintel GNPD, Jan. 2015, URL https://www.portal.mintel.com.

* cited by examiner

TWO COMPONENT HAIR TREATMENT KIT COMPRISING A HAIR COLORING CREAM AND A DEVELOPER COMPOSITION COMPRISING A SPECIFIC TENSIOACTIVE COMPOUND

CROSS-REFERENCE TO RELATED APPLICATIONS

This application is a U.S. National Phase of International PCT Application No. PCT/EP2018/057811 filed Mar. 27, 2018, the contents of the application are incorporated herein by reference in their entirety.

The present invention relates to a kit, preferably for coloring keratin fibers, the kit comprising in spatially separated form at least two kit components: A) a first kit component comprising at least these constituents: at least one alkaline agent; at least one amino acid; at least one organic phosphate ester compound selected from the group consisting of a monoester of a phosphate of one or more alkoxylated fatty alcohols, a diester of a phosphate of one or more non-alkoxylated fatty alcohols, and a mixture of both; water; and optionally at least an oxidative dye; and B) a second kit component comprising at least these constituents: at least one emulsifier; hydrogen peroxide; at least one fatty alcohol; and water; wherein the emulsifier is described by formula (I),

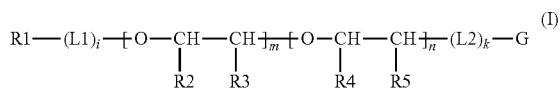

wherein R1 represents a saturated or unsaturated, linear or branched C7-C24 chain; L1 is a linking group and represents a carbonyl or a sulfonyl group; R2, R3, R4, R5 represent each individually a hydrogen atom or a methyl group, wherein at least one of R2 or R3 is a hydrogen atom, and wherein at least one of R4 or R5 is a hydrogen atom; L2 is a linking group independent from L1 and is selected from the group consisting of a carbonyl group, a carboxylic ester group, a sulfonyl group, a sulfonic ester group, a phenylene group or a —OCH$_2$—CH(OH)—CH$_2$— group; i, k, are independent from each other and can have an integer value of 0 or 1; m and n are each independent from each other and can have an integer value of 0 or a positive integer of 1 or more; G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof. The invention relates also to a process of manufacturing a composition which is the second kit component, a composition obtainable by such process, a ready-to-use composition, a way of preparing such and to a use of an emulsifier as in formula (I) and defined above in combination with the organic phosphate ester compound defined above to reduce the viscosity of hair coloring creams.

Cosmetic compositions based on oxidative dyes are well established in coloring keratin fibers, in particular of human hair, because of their intensive coloring and advantageous long-lasting color results. Such cosmetic compositions normally comprise one or more oxidative dye precursors, so-called primary intermediates, and one or more color-coupling agents. Practitioners in the hair treating business usually do not differentiate between primary intermediates and couplers by referring to them cumulatively as "dyes". However, these compounds are by themselves colorless to off-white. Almost identical compositions, but without the dyes, are also known and are used for the bleaching of hair.

Preparation to color hair include activation of a first component comprising primary intermediates and couplers. This activation is achieved by mixing the first component with second component, which is an oxidant. When this mixture is applied to hair fibers, the mixture forms the final dye(s) inside the hair fibers. Normally the first component is a carrier containing the dyes and is available in the form of a high viscosity cream. The second component, the oxidant, comprising hydrogen peroxide is often a fluid or an emulsion-forming aqueous solution.

The advantage of such a binary system is that it is versatile and useful for both conventional usage situations: the professional application by a hair stylist, as well as hair coloring by an individual at home. However, for these two usage situations differences exist in the design of the two component hair coloring compositions. The first component for the professional use normally consists of a highly viscous cream, which is mixed with the oxidants in a bowl by means of a brush prior to applying it to hair. The mixed coloring composition retains approximately the viscosity of the first component cream. This is of particular advantage to obtain complete and even color results, since a highly viscous cream can be applied to the hair in a thick layer by a brush.

Individuals at home, by contrast, often prefer bottle applicators, wherein a creamy first component comprising dyes is mixed with the oxidant by combining both components in an applicator bottle and applying shear forces by shaking the bottle to obtain the ready-to-use mixture. The applicator bottles contain a nozzle or a comb like rack of nozzles to control the amount and placement of the hair color composition. The requirement for such an application is that it has a sufficiently low viscosity so that the components are well mixable in the bottle by shaking to create a homogeneous, flowable, spreadable, but still substantially drip-free composition. Hence the viscosity for home use application with an applicator bottle is substantially lower than for a professional hair color application by brush.

From the practical side, mixing a highly viscous cream with a medium viscous oxidant is easy by means of brush and bowl. Mixing of a low viscosity cream with a low viscosity oxidant is also easy by means of shaking in a bottle applicator. However, mixing of a component having a viscosity initially designed for professional use, e.g. a viscous cream, with a component designed for home use, e.g. a low viscosity oxidant, in a bottle, may lead to poor mixing results, unfavorable on-head properties and unpredictable coloring results.

Accordingly, manufacturers of hair colorants usually produce dye compositions and oxidants, wherein the consistency of components for professional users, essentially the color creams, is different from components for home users. This causes additional complexity for the manufacturers because a variety of different formulations has to be developed for the same color shade, which are suitable either for application with a brush and a bowl or for the application with an applicator bottle. Moreover, a larger number of compositions conventionally require a larger number of raw materials, additional storage space and, thus, cause an economic and ecologic disadvantage.

Over the last decades, considerable progress has been made in the design of color cream components. Initially the key primary intermediate for numerous shades was p-phenylenediamine which was available as free base. The stability of most dye creams comprising mainly p-phenylenediamine against phase separation was given.

Later on toluene-2,5-diamine sulfate was used to replace p-phenylenediamine. However, dye creams based on toluene-2,5-diamine sulfate were often instable towards higher dye concentrations and separated into a wax and an aqueous phase. Considerable salt concentrations are generated by the neutralization of the sulfuric acid moiety in toluene-2,5-diamine sulfate, e.g. by added ammonia and monoethanolamine, respectively. Progress in the stability of color cream components has been achieved by using fatty alcohols in combination with anionic tensioactive compounds such as sodium lauryl alcohol diglycol ether sulfate as e.g. described by EP0594811B1.

An approach of reducing the number of formulas to serve professional and home hair coloring procedures is described by EP0650718B1. However, the developer system was tailor-made for a hair dye-containing carrier cream which had the inconvenience of not being able to absorb high salt loads which are introduced, e.g. by alkalizing agents, which are useful to replace at least some ammonia such as ammonium sulfate, ammonium chloride, ammonium bicarbonate, ammonium carbonate, ammonium carbamate or combinations thereof with one or more amino acids. Another inconvenience of the carrier described in this publication is the pronounced incompatibility towards cationic components such as care additives or other cationic ingredients.

Although stability of the color cream component was adequate for dissolving dyes available as adducts with an acid, the desire of cosmetic chemists was also to add further ingredients as alkalizing agents in order to partly or entirely replace ammonia because of its pungent smell. Moreover, the color cream should also be able to absorb larger amounts of carbonates such as ammonium carbonate, ammonium bicarbonate, ammonium carbamate, or for instance ammonium chloride, ammonium sulfate or an ammonium phosphate salt to enhance hair lightening performance.

These requirements were solved by using a combination of Cetearyl alcohol, Dicetyl Phosphate and Ceteth-10 Phosphate, which give non-sticky cream compositions able to accept considerable salt concentrations. Such a system has outstanding robustness towards dyes and alkalizers, both generating high salt concentration upon formulation. The combination of Cetearyl Alcohol with Dicetyl Phosphate and Ceteth-10 Phosphate is commercialized under the trade name Crodafos CES, available from Croda International Plc., Snaith, UK.

However, the design of appropriate developer compositions, which are selected and recommended for activating the dyes present in the Dicetyl Phosphate and Ceteth-10 Phosphate compositions remained relatively simple, as illustrated by the examples of US 2003/0226217 A1. The activators comprise hydrogen peroxide, the usual stabilizing agents, as well as a combination of waxes and polyethyleneglycol-monoalkylethers, wherein the monoalkyl group is a cetyl or stearyl alcohol group which was reacted with approximately 20-200 equivalents of ethyleneoxide. Typical examples of tensio active compounds used for such developer compositions are Ceteareth-25 and Steareth-100.

Despite all efforts of the past to provide cosmetic hair coloring compositions which satisfy the customers' as well as the hairdressers' needs, there is an ongoing need for further development in this area to satisfy the markets' needs.

A first object of the present invention is to provide a cosmetic hair coloring composition which overcomes at least one, preferably two or more of the disadvantages which were described with regard to art.

Another object of the invention is to provide a cosmetic hair coloring composition for the treatment of hair, in particular coloring, which is well accepted by model home users and clients of hair dressers.

Another object of the invention is to provide a cosmetic hair coloring composition which can be applied to, worked on and rinsed off the keratin fibers, e.g. hair, with ease.

Another object of the invention is to provide a cosmetic hair coloring composition which does not cause significant damage to keratin fibers.

Another object of the invention is to provide a cosmetic hair coloring composition which can be used for permanent lightening and coloring of keratin fibers.

Another object of the present invention is to provide a process for the manufacture of a cosmetic hair coloring composition.

Another object of the invention is to provide cosmetic hair coloring compositions and developers with which the overall number of compositions of a product line can be reduced.

Another object of the invention is to provide a developer composition, which can be employed by home user in a kit where the hair coloring cream has the characteristics of a professional cream.

Another object of the invention is to provide a developer composition which can be employed with professional hair coloring cream type in an applicator bottle.

Another object of the invention is to provide a kit of components for the treatment and/or coloring of hair, which can be easily used to prepare an easy-to-use ready-to-use treatment and/or coloring composition.

Another object of the invention is to provide a kit of components for the treatment and/or coloring of hair, from which a homogeneous ready-to-use composition can be produced.

Another object of the invention is to provide a kit of components for the treatment and/or coloring of hair, from which a homogeneous ready-to-use composition can be produced by nonprofessional, home users.

Another object of the invention is to provide a kit of components for the treatment and/or coloring of hair, from which a homogeneous ready-to-use composition can be produced that can be easily distributed on the hair.

Another object of the invention is to provide a kit of components for the treatment and/or coloring of hair, which is ammonia free.

Another object of the invention is a process of manufacturing a developer composition for home users, preferably in combination with professional hair coloring cream.

A contribution to the solution of at least one of the above objects is provided by the subject-matter of the category-forming embodiments. The dependent sub-embodiments of the category-forming embodiments represent preferred embodiments of the invention, the subject-matter of which also makes a contribution to solving at least one of the objects mentioned above.

PREFERRED EMBODIMENTS

[1] A kit, preferably apt to color keratin fibers, the kit comprising in spatially separated form at least two kit components:

A) a first kit component comprising at least these constituents:
   A-a) at least one alkaline agent;
   A-b) at least one amino acid;
   A-c) at least one organic phosphate ester compound selected from the group consisting of a monoester of a phosphate of one or more alkoxylated fatty alcohols, a diester of a phosphate of one or more non-alkoxylated fatty alcohols, and a mixture of both;
   A-d) water;
   A-c) optionally at least an oxidative dye and/or a direct dye
B) a second kit component comprising at least these constituents:
   B-a) at least one emulsifier;
   B-b) hydrogen peroxide;
   B-c) at least one fatty alcohol;
   B-d) water;
wherein the at least one emulsifier is described by formula (I),

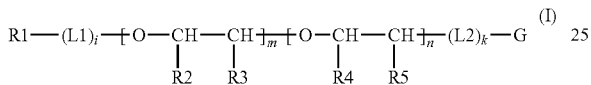

wherein
R1 represents a saturated or unsaturated, linear or branched C7-C24 chain;
L1 is a linking group and represents a carbonyl or a sulfonyl group;
R2, R3, R4, R5 represent each individually a hydrogen atom or a methyl group,
   wherein at least one of R2 or R3 is a hydrogen atom, and
   wherein at least one of R4 or R5 is a hydrogen atom;
L2 is a linking group independent from L1 and is selected from the group consisting of
   a carbonyl group, a carboxylic ester group, a sulfonyl group, a sulfonic ester group,
   a phenylene group or a —OCH$_2$—CH(OH)—CH$_2$— group;
i, k, are independent from each other and can have an integer value of 0 or 1;
m and n are each independent from each other and can have an integer value of at least 0;
G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

[2] The kit according to embodiment [1], wherein the organic phosphate ester compound comprises at least Dicetyl Phosphate and Ceteth-10 Phosphate.

[3] The kit according to embodiment [1] or [2], wherein the emulsifier of the second kit component is nonionic and selected from the group consisting of PEG-20 sorbitan monolaurate (Tween 20), PEG-4 sorbitan monolaurate (Tween 21), PEG-20 sorbitan monopalmitate (Tween 40), PEG-20 sorbitan monostearate (Tween 60), PEG-4 sorbitan monostearate (Tween 61), PEG-20 sorbitan monooleate (Tween 80), alkoxylated alkyl glyceryl ether sulfonates and a combination of two or more thereof; a preferred nonionic emulsifier is PEG-20 sorbitan monolaurate (Tween 20) is most preferred.

[4] The kit according to embodiment 1 or [2], wherein the emulsifier of the second kit component is nonionic and selected from the group consisting of sorbitan monolaurate (Span 20), sorbitan monopalmitate (Span 40), sorbitan monostearate (Span 60), sorbitan monooleate (Span 80), Sorbitan isostearate (Span 120) and a combination of two or more thereof; a preferred nonionic emulsifier is Sorbitan monolaurate.

[5] The kit according to embodiment 1 or [2], wherein the emulsifier of the second kit component is anionic and selected from the group consisting of Sodium dinonylnaphthalene sulfonate, Sodium 4-ethyl-1-(3-ethylpentyl)-1-octyl sulfate, Sodium dodecylbenzene sulfonate, Sodium lauryl sulfate; Sodium myristyl sulfate, Sodium dodecyl sulfate, Sodium cetyl sulfate, Sodium stearyl sulfate; Sodium cocoyl isethionate, Sodium myristoyl isethionate; mono and dialkyl sulfosuccinates, such as Disodium lauryl sulfosuccinate; disodium laureth sulfosuccinate, Disodium stearyl sulfosuccinate, Sodium dihexyl sulfosuccinate and Sodium dioctyl sulfosuccinate, and a combination of two or more thereof.

[6] The kit according to embodiment 1 or [2], wherein the emulsifier of the second kit component is cationic and selected from the group consisting of Cetrimonium chloride, Cetrimonium methosulfate, and Soytrimonium chloride.

[7] The kit according to any one of the preceding embodiments, wherein the second kit component comprises in the range from 0.1 to 10 weight-% of the emulsifier, based on the total weight of the second kit component.

[8] The kit according to any one of the preceding embodiments, wherein the kit is characterized by at least one of these features:
(A) A total amount of the organic phosphate ester compounds of the first kit component is in the range from 0.1 to 10 wt.-%, based on total weight of the first component;
(B) A total amount of the amino acid of the first kit component is in the range from 0.5 to 20 wt.-%, based on total weight of the first component;
(C) A total amount of the alkaline agent of the first kit component is in the range from 1 to 15 wt.-%, based on total weight of the first component;
(D) A total amount of one or more oxidation dyes of the first kit component is in the range from 0 to 10 wt.-%, based on total weight of the first component;
(E) A total amount of the hydrogen peroxide of the second kit component is in the range from 0.5 to 12 wt.-%, based on total weight of the second component;
(F) A total amount of the fatty alcohol of the second kit component is in the range from 0.1 to 10 wt.-%, based on total weight of the second component;
(G) A total amount of the emulsifiers of the second kit component is in the range from 0.1 to 10 wt.-%, based on total weight of the second component;
or a combination of two or more of (A), (B), (C), (D), (E), (F) and (G).

[9] The kit according to any one of the preceding embodiments, wherein the kit is characterized by at least one of these features:

(a) the first kit component has a pH in the range from 7.0 to 12; preferably in the range from 9.0 to 10.5;
(b) the second kit component has a pH in the range from 2.0 to 4.0; preferably in the range from 2.5 to 3.0;
(c) wherein the weight ratio of the first kit component to the second kit component in the kit is in the range from 2:1 to 1:3.

[10] The kit according to any one of the preceding embodiments, wherein the amino acid of the first kit component is selected from the group consisting of glycine, serine, asparagine, threonine, glutamine, arginine, lysine, α- or β-alanine, and a combination of two or more thereof.

[11] The kit according to any one of the preceding embodiments, wherein the alkaline agent of the first kit component is selected from the group consisting of ammonium hydroxide, monoethanolamine (MEA), diethanolamine, triethanolamine, monopropanolamine, dipropanolamine, tripropanolamine, 2-amino-2-methyl-1,3-propanediol (AMPD), 2-amino-2-ethyl-1,3-propanediol (AEPD), 2-amino-2-methyl-1-propanol (AMP), 2-amino-2-hydroxymethyl-1,3-propanediol (TRIS), sodium and potassium hydroxide, ammonium carbonate, ammonium bicarbonate, ammonium carbamate, and a combination of two or more thereof. A preferred alkaline agent is 2-amino-2-hydroxymethyl-1,3-propanediol (TRIS).

[12] The kit according to any one of the preceding embodiments, wherein the first kit component comprises at least one oxidative dye, which is selected from the group of p-Phenylenediamines, p-Aminophenols, 4,5-Diaminopyrazoles, Pyrimidines, Resorcinols, m-Phenylenediamines, o-Aminophenols, m-Aminophenols, 1-Naphthols, Pyridines, Indoles, Indolines, and a combination of two or more thereof.

[13] The kit according to any one of the preceding embodiments, wherein the at least one fatty alcohol of the second kit component comprises from 8 to 30 carbon atoms, preferably at least one fatty alcohol selected from the group consisting of Cetyl alcohol, Stearyl alcohol, Octyldodecanol, 2-Butyloctanol, 2-Hexyldeanol, 2 Undecylpentadecanol, Oleyl alcohol, Linoleyl alcohol, and a combination of two or more thereof

[14] A process of manufacturing a composition, preferably apt to color keratin fibers, wherein the composition is the second kit component in any one of embodiments [1] to [13], wherein the process comprises at least these steps:
  i) Providing the at least one fatty alcohol, and an amount of water;
  ii) Mixing the at least one fatty alcohol and the amount of water to form an emulsion precursor;
  iii) Providing and adding to the emulsion precursor an amount of hydrogen peroxide and the at least one emulsifier to form a pre-emulsion; wherein the at least one emulsifier is defined by formula (I);
  iv) Adjusting the pH of the pre-emulsion to a value in the range from 2 to 4.

[15] A composition obtainable by a process according to embodiment [14].

[16] A composition, preferably arranged in a two component kit and apt to color keratin fibers, the composition comprising at least these constituents:
  B-a) at least one emulsifier;
  B-b) hydrogen peroxide;
  B-c) at least one fatty alcohol;
  B-d) water;
  wherein the emulsifier is described by formula (I),

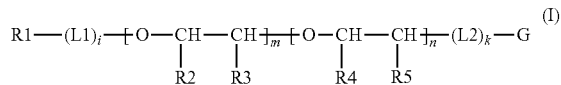

wherein
  R1 represents a saturated or unsaturated, linear or branched C7-C24 chain;
  L1 is a linking group and represents a carbonyl or a sulfonyl group;
  R2, R3, R4, R5 represent each individually a hydrogen atom or a methyl group,
    wherein at least one of R2 or R3 is a hydrogen atom, and
    wherein at least one of R4 or R5 is a hydrogen atom;
  L2 is a linking group independent from L1 and is selected from the group consisting of a carbonyl group, a carboxylic ester group, a sulfonyl group, a sulfonic ester group, a phenylene group or a —OCH$_2$—CH(OH)—CH$_2$— group;
  i, k, are independent from each other and can have an integer value of 0 or 1;
  m and n are each independent from each other and can have an integer value of at least 0;
  G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

[17] A kit, preferably apt to color keratin fibers, comprising in spatially separated form at least a first and second kit component, wherein the second kit component comprises a composition according to any one of embodiments [14] to [15].

[18] A ready-to-use composition, preferably apt to color keratin fibres, wherein the ready-to-use composition is obtainable by mixing the kit components of the kit according to any one of embodiments [1] to [13] and [17]. Preferably, the mixing is done directly prior to application.

[19] A process of preparing a ready-to-use composition, which is apt to color keratin fibers, wherein the process comprises at least these steps:
  (i) Providing a kit according to any one of embodiments [1] to [3] and [17],
  (ii) Mixing the kit components.

[20] The process of embodiment [19], wherein at least the mixing is performed in a bottle, preferably an applicator bottle.

[21] The process of embodiment [19], wherein at least the mixing is performed in a bowl, wherein a mixing tool or a hair color application tool, preferably an applicator brush, is used.

[22] The ready-to-use composition according to any one of embodiments [18] to 21, wherein the ratio of the first kit component and the second kit component is in the range of from 2:1 to 1:3, each number based on parts by weight.

[23] A process for coloring keratin fibers, comprising the steps of:
  I. providing keratin fibers;
  II. contacting the keratin fibers of step I. with a ready-to-use composition according to embodiment [18] or with a ready-to-use composition obtainable by a process according to any one of embodiment [19] to [2];
  III. optionally rinsing the keratin fibers;
  IV. optionally drying the keratin fibers.
[24] The process of embodiment [23], wherein the first kit component and the second kit component are provided in a weight ratio of the first kit component and the second kit component in the range from 2:1 to 1:3, each number based on parts by weight.
[25] A use of an emulsifier in combination with at least one organic phosphate ester compound to reduce the viscosity of a hair coloring composition,
  wherein the emulsifier is described by formula (I),

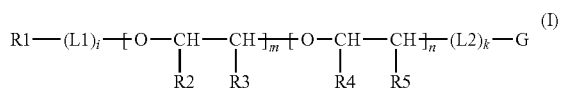

wherein
  R1 represents a saturated or unsaturated, linear or branched C7-C24 chain;
  L1 is a linking group and represents a carbonyl or a sulfonyl group;
  R2, R3, R4, R5 represent each individually a hydrogen atom or a methyl group,
    wherein at least one of R2 or R3 is a hydrogen atom, and
    wherein at least one of R4 or R5 is a hydrogen atom;
  L2 is a linking group independent from L1 and is selected from the group consisting of a carbonyl group, a carboxylic ester group, a sulfonyl group, a sulfonic ester group, a phenylene group or a —OCH$_2$—CH(OH)—CH$_2$— group;
  i, k, are independent from each other and can have an integer value of 0 or 1;
  m and n are each independent from each other and can have an integer value of at least 0; wherein the sum of m and n is different from 0.
  G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

DEFINITIONS

The term "in the range from x to y" is understood in the present context to comprise all values between the number x and y, and also the limit forming numbers x and y. For example, the term "in the range from 2 to 13" comprises the numbers 2, 13 and all in between.

The term "in a weight ratio of X to Y is in the range from x1:y1 to x2:y2" is understood in the present context that constituents X and Y can be present in the following range, including the mentioned values: from x1 parts X and y1 parts Y to x2 parts X and y2 parts Y. For example, the term "a weight ratio of the first kit component to the second kit component is in the range from 2:1 to 1:3" describes a ratio beginning with from 2 parts of the first kit component to 1 part of the second kit component up to 1 part of the first kit component to 3 parts of the second kit component.

A radical described as a Cx-Xy chain is understood to describe a carbon radical comprising x to y C-atoms in a chain. Unless otherwise particularly specified, the chain can be linear or branched, saturated and unsaturated. For example, a radical R1 which represents a C7-C24 chain describes a radical with a chain of 7 to 24 carbon atoms.

Chemical compounds can be followed by an expression in brackets. In this event, the bracket mention a trademarks for illustrative purposes, under which the chemical compound can be purchased. For example: sorbitan monolaurate (TWEEN 20).

DETAILED DESCRIPTION OF THE INVENTION

A first aspect of the invention is a kit, which is preferably designed for coloring keratin fibers, in particular those of humans or pet animals, wherein the kit comprises in spatially separated form at least two kit components,
  A) a first kit component comprising at least these constituents:
    A-a) at least one alkaline agent;
    A-b) at least one amino acid;
    A-c) at least one organic phosphate ester compound selected from the group consisting of a monoester of a phosphate of one or more alkoxylated fatty alcohols, a diester of a phosphate of one or more non-alkoxylated fatty alcohols, and a mixture of both;
    A-d) water;
    A-e) optionally at least an oxidative dye and/or a direct dye;
  B) a second kit component comprising at least these constituents:
    B-a) at least one emulsifier;
    B-b) hydrogen peroxide;
    B-c) at least one fatty alcohol;
    B-d) water;
  wherein the emulsifier is described by formula (T),

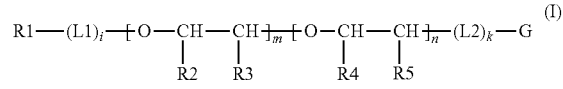

wherein
  R1 represents a saturated or unsaturated, linear or branched C7-C24 chain;
  L1 is a linking group and represents a carbonyl or a sulfonyl group;
  R2, R3, R4, R5 represent each individually a hydrogen atom or a methyl group, wherein at least one of R2 or R3 is a hydrogen atom, and wherein at least one of R4 or R5 is a hydrogen atom;
  L2 is a linking group independent from L1 and is selected from the group consisting of a carbonyl group, a carboxylic ester group, a sulfonyl group, a sulfonic ester group, a phenylene group or a —OCH$_2$—CH(OH)—CH$_2$— group;
  i, k, are independent from each other and can have an integer value of 0 or 1;

m and n are each independent from each other and can have an integer value of at least 0; often each m and each n does not exceed 10;

G is selected from the group consisting of sorbitan; a sorbitan where the hydroxy groups are partially or fully substituted by polyethyleneoxy chains; an anionic group selected from the group consisting of a sulfonic acid group, a sulphate group, a C1-alkylenesulfonic acid group, and a C2-alkylenesulfonic acid group; a cationic group which includes a quarternized ammonium cation and a combination of two or more thereof.

Oxidative hair coloring compositions like those according to the present invention are usually sold in kits comprising, in spatially separated form, for example individually packaged components, such as separate containers. In spatially separated form can also be achieved by a container which comprises two or more chamber. Such a two or more chambered container may have an opening for each chamber. The opening of at least two of the chambers can be at adjacent position, e.g. having a common screw around it, in order to accept a single dispenser on the screw, in which dispenser the components of at least two of the chamber are mixed while dispensing. In an alternative embodiment, the two or more chambered container can have some or all openings at distant positions. In this event, mixing of at least two of the kit components is likely to be performed in a mixing bowl. A first kit component usually contains the kit component comprising dyes, and an alkaline agent and; the second kit component usually contains a developer composition comprising the oxidizing agent. Often, hydrogen peroxide is used as oxidizing agent. Anyway, the consumer as well as the professional hair stylist mixes the first kit component and the second kit component prior to use, thereby, preparing a ready-to-use composition, which he then applies onto the hair. Preferably, the ready-to-use composition is prepared immediately prior to application.

The first kit component of the invention comprises at least one organic phosphate ester compound, which is selected from the group consisting of a monoester of a phosphate of one or more alkoxylated fatty alcohols, a diester of a phosphate of one or more non-alkoxylated fatty alcohols, and a mixture of both.

In a preferred embodiment of the invention, the first kit component comprises from 0.1 to 10 wt,-%, preferably 0.1 to 6 wt. %, or from 0.5 to 4 wt. %, or from 1 to 2.5 wt. % in total of the one or more organic phosphate ester compounds, each wt. % based on the total weight of the first kit component.

Turning to the chemical identity of the organic phosphate ester compound, numerous organic phosphate ester compounds with the aforementioned features are known in the art and appear useful in the present invention.

The monoester of phosphates of alkoxylated fatty alcohols of the composition according to the invention are composed of C12-C22 fatty alcohols alkoxylated with from 1 to 50 moles of an alkylene oxide, the number of moles of alkylene oxide with respect to the moles of fatty alcohol. Formula (1) is a general representation of an organic phosphate ester.

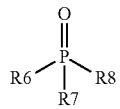

A monoester of phosphate of one or more alkoxylated fatty alcohols according to the invention is characterized as follows:

Rx with x=6, 7, 8 can be same or different and Rx is selected from:
aa) —OM, wherein M equals H, Na or K;
bb) —OR9, wherein R9 can be linear or branched and is a $C_1$-$C_{40}$ alkyl group, preferably $C_{12}$-$C_{22}$, or a $C_2$-$C_{40}$ alkenyl group, preferably $C_{12}$-$C_{20}$;
cc) —(OCH$_2$CH$_2$)$_n$OR9, wherein R9 has the same meaning as identified above, n is an integer in the range of from 1 to 50;

with the proviso that at least one group Rx is chosen according to aa) and at least another group is chosen according to bb) or cc).

In a further preferred embodiment, the monoester of phosphate is linear, more preferably it is defined by at least one alkyl group R9, wherein R9 is selected from the group consisting of $C_1$, $C_2$, $C_3$. $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$; R9 being preferably one of $C_{16}$, $C_{18}$, $C_{20}$, $C_{22}$.

In a further preferred embodiment, the monoester of phosphate is linear, more preferably it is defined by at least one alkenyl group R9, wherein R9 is selected from the group consisting of $C_2$, $C_3$. $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$; R9 being preferably one of $C_{16}$, $C_{18}$, $C_{20}$, $C_{22}$.

The diester of phosphates of non-alkoxylated fatty alcohols of the composition according to the invention are composed of C12-C22 non-alkoxylated fatty alcohols. With respect to formula (1), diester of phosphates of non-alkoxylated fatty alcohols according to the invention are characterized as follows:

Rx with x=6, 7, 8 can be same or different, and Rx is selected from:
aa) —OM, wherein M equals H, Na or K;
bb) —OR9, wherein R9 can be linear or branched and is a $C_1$-$C_{40}$ alkyl group, preferable $C_{12}$-$C_{22}$, or a $C_2$-$C_{40}$ alkenyl group, preferable $C_{12}$-$C_{20}$;

with the proviso that one group Rx is chosen according to aa) and two groups are chosen according to bb).

In a further preferred embodiment, the monoester of phosphate is linear, more preferably it is defined by at least one alkyl group R9, wherein R9 is selected from the group consisting of $C_1$, $C_2$, $C_3$. $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$; R9 being preferably one of $C_{16}$, $C_{18}$, $C_{20}$, $C_{22}$.

In a further preferred embodiment, the monoester of phosphate is linear, more preferably it is defined by at least one alkenyl group R9, wherein R9 is selected from the group consisting of $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$; R9 being preferably one of $C_{16}$, $C_{18}$, $C_{20}$, $C_{22}$.

Moreover, mixtures of the abovementioned phosphate esters can be employed. These mixtures can comprise two or more monoester of phosphates of alkoxylated fatty alcohols and one diester of phosphate of non-alkoxylated fatty alcohols, one monoester of phosphates of alkoxylated fatty alcohols and two or more diesters of phosphate of non-alkoxylated fatty alcohols, or a mixture of two or more monoesters of phosphates of alkoxylated fatty alcohols and two or more diesters of phosphate of non-alkoxylated fatty alcohols.

In a further preferred embodiment of the invention, the at least one organic phosphate ester compound is selected from the group consisting of dicetyl phosphate, ceteth-10 phosphate, oleth-5 phosphate and dioleyl phosphate. Yet more preferred is a combination of two or more of these phosphate esters, or even all of them. All names are provided according to INCI nomenclature.

Some preferred combinations of the above phosphate esters are commercially available from Croda International Plc, Snaith, United Kingdom, under the trade name CRODAFOS. These are, e.g.

Ceteth-10 phosphate and Dicetyl phosphate, as in CRODAFOS CES,
Ceteth-20 phosphate and dicetyl phosphate, as in CRODAFOS CS-20 ACID, and
Oleth-5 phosphate and Dioleyl phosphate, as in CRODAFOS HCE.

In a particularly preferred embodiment of the invention, the organic phosphate ester compound comprises at least Dicetyl Phosphate and Ceteth-10 Phosphate. A commercial product which is very suitable and fulfils this requirement is Crodafos CES®. Crodafos CES® is available for purchase from Croda International Plc, Snaith (United Kingdom). Crodafos CES® comprises these three components: Cetearyl alcohol (mixture of Cetyl alcohol and Stearyl alcohol), and dicetyl phosphate (CAS: 2197-63-9) and ceteth-10 phosphate (CAS: 50643-20-4).

In a preferred embodiment of the invention, the first kit component comprises from 0.1 to 10 wt,-%, preferably 0.1 to 6 wt. %, or from 0.5 to 4 wt. %, or from 1 to 2.5 wt. % in total of an organic phosphate ester compound comprising at least Dicetyl Phosphate and Ceteth-10 Phosphate, wherein the wt. % are the combined wt-% of all organic phosphate ester compounds in the first kit component, and the wt.-% are based on the total weight of the first kit component.

In a further preferred embodiment of the invention, the first kit component comprises from 0.1 to 10 wt,-%, preferably 0.1 to 6 wt. %, or from 0.5 to 4 wt. %, or from 1 to 2.5 wt. % in total of Crodafos CES®, the wt.-% are based on the total weight of the first kit component.

The first kit component of the invention further comprises at least one alkaline agent. The first kit component can contain alkaline agent in a range from 1 to 15 wt.-%, or from 2 to 10 wt.-%, yet more preferable from 2 to 8 wt.-%.

In general, all alkaline agents can be employed which are known in the art and appear suitable for the preparation of the composition of the invention. In a further preferred embodiment, the alkaline agent is selected from the group consisting of ammonium hydroxide, an alkanolamine such as monoethanolamine (MEA), diethanolamine, triethanolamine, monopropanolamine, dipropanolamine, tripropanolamine, 2-amino-2-methyl-1,3-propanediol (AMPD), 2-amino-2-ethyl-1,3-propanediol (AEPD), 2-amino-2-methyl-1-propanol (AMP), 2-amino-2-hydroxymethyl-1,3-propanediol (TRIS), sodium and potassium hydroxide, ammonium carbonate, ammonium bicarbonate, ammonium carbamate, and a combination of two or more thereof.

The first kit component of the invention further comprises at least one amino acid. In general, all amino acids can be employed which are known in the art. In the present invention, the term amino acid comprises free amino acids, salts of amino acid, e.g. sodium or potassium salt with regard to the cation, as well as halides on behalf of the anion, if applicable. Preferred amino acids are selected from the group consisting of glycine, serine, asparagine, threonine, glutamine, arginine and lysine as well as α- and β-alanine, and mixtures of two or more compounds thereof. Smaller amino acids are more preferred than larger ones; wherein small and large refer to the molecular weight of the amino acid. Salts of amino acids, such as sodium or potassium salts of amino acids, are not considered as alkaline agents in the context of the present invention.

In a preferred embodiment of the invention, the cosmetic composition comprises a total of from 0.1 to 20 wt. %, preferably from 1.0 to 15 wt. %, or from 2.0 to 15 wt. %, or from 6 to 12 wt. % of one or more amino acids, each wt. % based on the total weight of the first kit component.

In a further preferred embodiment, the first kit component can optionally comprise at least one dye. The at least one dye is preferably selected from
(a) at least one primary intermediate, and optionally further at least one color coupling agent;
(b) at least one direct dye; and
(c) mixtures of (a) and (b).

A number of dyes can be used in the first kit component of the invention. Preferred dyes are oxidative dyes selected from primary intermediates. Direct dyes are another preferred group of dyes useful in the first kit component. Direct dyes are considered particularly useful for generating particular shades or reflexes. The direct dyes of the embodiment are preferably selected from the group consisting of nitro dyes, azo dyes, anthraquinone dyes and triphenylmethane dyes, each of which can be neutral, cationic, anionic or zwitterionic (also referred to as: "bipolar ion").

Regarding alternative (a), numerous primary intermediates are known to and considered suitable by those skilled in the art. In a preferred embodiment, the composition of the invention comprises a total amount of dyes in the range of from 0.001 to 12 wt. %, preferably in the range of from 0.01 to 10 wt. %, yet more preferably in the range of from 0.01 to 8 wt. %, in total of one or more dyes, each based on the total weight of the composition.

Preferred primary intermediates are selected from the group consisting of p-Phenylenediamines, p-Aminophenols, o-Aminophenols, 4,5-Diaminopyrazoles, Pyrimidines. Yet more preferred are 1,4-diamino-benzene; 1,4-diamino-2-methyl-benzene; 1,4-diamino-2-(2-hydroxyethyl)-benzene; 1,4-diamino-2,3-dimethyl-benzene; 1,4-diamino-2,6-dimethylbenzene; 1,4-diamino-2-methoxymethyl-benzene; 1,4-diamino-2-chloro-benzene; 4-[di(2-hydroxyethyl)amino]-aniline; 2,2'-{2-[(4-aminophenyl)amino]ethyl}imino)diethanol; (4-aminophenyl)-(3-(imidazol-1-yl)propyl)amine; N,N'-bis((3-hydroxyethyl)-N,N'-bis(4'-aminophenyl)-1,3-diaminopropanol; 4-aminophenol; 4-amino-3-methylphenol; bis(5-amino-2-hydroxyphenyl)methane; 2-amino-5-ethylphenol; 4,5-diamino-1-(2-hydroxyethyl)-1H-pyrazole; 2,3-diaminodihydroxypyrazolo pyrazolone dimethosulfonate; 2,4,5,6-tetraaminopyrimidine; 2,5,6-Triamino-4-pyrimidinol; and a combination of two or more thereof. The primary intermediates can also be present in adduct form with an acid, e.g. hydrochloric acid or sulfuric acid. 1,4-diamino-2-methoxymethyl-benzene is a particularly preferred choice of one primary intermediate.

Though not absolutely necessary, at least one color coupling agent is often added to the at least one primary amine. It is a further embodiment of the present invention for alternative (a) to combine at least one primary intermediate with at least one color coupling agent. Preferred color coupling agents are selected from the group consisting of 1,3-dihydroxybenzene; 4-chloro-1,3-dihydroxybenzene; 1,3-dihydroxy-2-methylbenzene; 3-aminophenol; 5-amino-2-methylphenol; 5-amino-4-chloro-2-methylphenol; 3-amino-2,6-dimethylphenol; 2-methyl-5-hydroxyethylaminophenol; 3-amino-2,4-dichlorophenol; 3,4-dihydro-2H-1,4-benzoxazin-6-ol; N-hydroxyethyl-3,4-methylenedioxyaniline; 3,4-dihydro-6-hydroxy-2H-1,4-benzoxazine; 6-amino-3,4-dihydro-2H-1,4-benzoxazine; 2,4-diamino-1-

(2-hydroxyethoxy)benzene; 2-amino-4-[(2-hydroxyethyl)amino]anisole; 1,3-bis(2,4-diaminophenoxy)propane; 1-methyl-2,6-bis-(2-hydroxyethylamino)-benzene; 1-naphthol; 2-methyl-1-naphthol; 1,5-naphthalenediol; 2,7-naphthalenediol; 2,6-diaminopyridine; 2,6-dihydroxy-3,4-dimethylpyridine; 3,5-diamino-2,6-dimethoxypyridine; 2-amino-3-hydroxypyridine; 6-methoxy-2-methylamino-3-aminopyridine; 3-methyl-1-phenyl-5-pyrazolone; 6-hydroxyindole; 5,6-dihydroxyindole; and a combination of two or more thereof.

Color coupling agents which have one or two amino groups can be present as free amines, or partially or totally in adduct form with an acid, e.g. as adduct with hydrochloric acid or sulfuric acid.

Preferred nitro dyes are selected from the group consisting of 2-Amino-3-nitrophenol; 2-[(2-Hydroxyethyl)amino]-1-methoxy-5-nitrobenzene; 1-(2-Hydroxyethoxy)-3-methylamino-4 nitrobenzene; 2,3-(Dihydroxypropoxy)-3-methylamino-4-nitrobenzene; 1-[(2-Ureido ethyl)amino]-4-nitrobenzene; 4-[(2-Hydroxyethyl)amino]-3-nitro-1-methylbenzene; 1-[(2-Hydroxyethyl)amino]-2-nitrobenzene (HC Yellow No. 2); 1-(2-Hydroxyethoxy)-2-[(2-hydroxyethyl)amino]-5-nitrobenzene (HC Yellow No. 4); 1-Amino-2-[(2-hydroxyethyl)amino]-5-nitrobenzene (HC Yellow No. 5); 4-[(2,3-Dihydroxypropyl)amino]-3 nitro-1-trifluoromethylbenzene (HC Yellow No. 6); 3-[(2-Amino ethyl)amino]-1-methoxy-4-nitrobenzene hydrochloride (HC Yellow No. 9); 1-Chloro-2,4-bis-[(2-hydroxyethyl)amino]-5-nitrobenzene (HC Yellow No. 10); 2-[(2-Hydroxyethyl)amino]-5-nitrophenol (HC Yellow No. 11); 1-Chloro-4-[(2-hydroxyethyl)amino]-3-nitrobenzene (HC Yellow No. 12); 4-[(2-Hydroxyethyl)amino]-3-nitro-1-trifluoromethyl-benzene (HC Yellow No. 13); 4-[(2-Hydroxyethyl)amino]-3-nitro-benzonitrile (HC Yellow No. 14); 4-[(2-Hydroxyethyl)amino]-3-nitro-benzamide (HC Yellow No. 15); 1,4-diamino-2-nitrobenzene; 1,4-Bis[(2-hydroxyethyl)amino]-2-nitrobenzene; 2-Amino-4,6-dinitro-phenol; 4-Amino-3-nitrophenol; 1-Amino-5-chloro-4-[(2-hydroxyethyl)amino]-2-nitrobenzene; 4-[(2-Hydroxyethyl)amino]-3 nitrophenol; 1[(2-Aminoethyl)amino]-4-(2-hydroxyethoxy)-2-nitrobenzene (HC Orange No. 2); 4-(2,3-Dihydroxypropoxy)-1-[(2-hydroxyethyl)amino]-2-nitrobenzene (HC Orange No. 3); 2-[(2-Hydroxyethyl)amino]-4,6-dinitro-phenol; 4-Ethylamino-3-nitrobenzoic acid; 2-[(4-Amino-2-nitrophenyl)amino]-benzoic acid; 2-Chloro-6-ethylamino-4-nitrophenol; 2-Amino-6-chloro-4-nitrophenol; 4-[(3-Hydroxypropyl)amino]-3-nitrophenol; 2,5-Diamino-6-nitropyridine; 1,2,3,4-Tetrahydro-6-nitroquinoxaline; 4-Amino-2-nitro-diphenylamine (HC Red No. 1); 4-Amino-1-[(2-hydroxyethyl)amino]-2-nitrobenzene (HC Red No. 3); 1-Amino-4-[(2-hydroxyethyl)amino]-2-nitrobenzene (HC Red No. 7); 1-Amino-5-chloro-4-[(2,3-dihydroxypropyl)amino]-2-nitrobenzene (HC Red No. 10); 5-Chloro-1,4-[di(2,3-dihydroxypropyl)amino]-2-nitrobenzene (HC Red No. 11); 1-Amino-4-[di(2-hydroxyethyl)amino]-2-nitrobenzene hydrochloride (HC Red No. 13); 7-Amino-3,4-dihydro-6-nitro-2H-1,4-benzoxazine (HC Red No. 14); 1-Amino-3-methyl-4-[(2-hydroxyethyl)amino]-6-nitrobenzene (HC Violet No. 1); 1-(3-Hydroxypropylamino)-4-[di(2-hydroxyethyl)amino]-2-nitrobenzene (HC Violet No. 2); 1-(2-Hydroxyethyl)amino-2-nitro-4-[di(2-hydroxyethyl)amino]-benzene (HC Blue No. 2); 1-Methylamino-4-[methyl-(2,3-dihydroxypropyl)amino]-2-nitrobenzene (HC Blue No. 6); 1-[(2,3-Dihydroxypropyl)amino]-4-[ethyl-(2-hydroxyethyl)amino]-2-nitrobenzene hydrochloride (HC Blue No. 9); 1-[(2,3-Dihydroxypropyl)amino]-4-[methyl-(2-hydroxyethyl)amino]-2-nitrobenzene (HC Blue No. 10); 4-[Di(2-hydroxyethyl)amino]-1-[(2-methoxyethyl)amino]-2-nitrobenzene (HC Blue No. 11); 4-[Ethyl-(2-hydroxyethyl)amino]-1-[(2-hydroxyethyl)amino]-2-nitrobenzene hydrochloride (HC Blue No. 12); 2-((4-Amino-2-nitrophenyl)amino)-5-dimethylaminobenzoic acid (HC Blue No. 13), and combinations of two or more thereof.

Preferred cationic dyes are selected from the group consisting of Basic Yellow 57, Basic Brown 16, Basic Brown 17, Basic Red 76, Basic Red 118, Basic Blue 99, Basic Yellow 87, Basic Orange 31, Basic Red 51, Basic Violet 2, Basic Blue 75, Basic Blue 77, Basic Blue 124, HC Blue 15, HC Blue 16, HC Blue 17, and combinations of two or more thereof.

Two or more of the above mentioned dyes and/or color coupling agent-primary intermediate combinations, or combinations of one or more dyes with one or more combinations of color coupling agent and primary intermediate can be used according to a further preferred embodiment.

The second kit component of the invention comprises at least one emulsifier, hydrogen peroxide, at least one fatty alcohol, and optionally a further dose of water. Water in the second kit component can either originate from providing hydrogen peroxide in aqueous solution, or be added separately as a further dose, e.g. in form of deionized water.

The emulsifier of the invention and in the second kit component can be defined by formula (I)

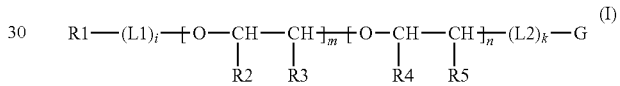

wherein
R1 represents a saturated or unsaturated, linear or branched C7-C24 chain; preferably, R1 is a linear C7-C24 chain;
L1 is a linking group and represents a carbonyl (>C=O) or a sulfonyl group (>S(=O)$_2$);
R2, R3, R4, R5 represent each individually a hydrogen (—H) atom or a methyl group (—CH$_3$),
  wherein at least one of R2 or R3 is a hydrogen atom,
  wherein at least one of R4 or R5 is a hydrogen atom;
  preferably, R2 and R3 can be —H; or R2 is —H and R3 is —CH$_3$; or R2 is —CH$_3$ and R3 is —H;
  preferably, R4 and R5 can be —H; or R4 is —H and R5 is —CH$_3$; or R4 is —CH$_3$ and R5 is —H;
  yet more preferred, R2 and R4 are —CH$_3$ and R3 and R5 are —H; or R2 and R4 are —H and R3 and R5 are —CH$_3$;
L2 is a linking group independent from L1 and is selected from the group consisting of a carbonyl group (>C=O), a carboxylic ester group (—C(=O)O—), a sulfonyl group (>S(=O)$_2$), a sulfonic ester group (—S(=O)$_2$O—), a phenylene group or a —OCH$_2$—CH(OH)—CH$_2$— group;
i, k, are independent from each other and can have an integer value of 0 or 1; preferably i and k=0, or i=0 and k=1; or i=1 and k=0; or i and k=1;
m and n are each independent from each other and can have an integer value of at least 0; often, a value of 10 is not exceed for each m, n individually; preferably each m, n can be individually selected from 0, 1, 2, 3, 4, 5, 6, 7, 8, 9 and 10;
G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

In a preferred embodiment, the emulsifier of the invention is present in an amount in the range from 0.1 to 10 wt.-%, or from 0.5 to 7 wt.-%, or from 0.1 to 5 wt. %, or from 1 to 5 wt.-%, each wt.-% based on the total weight of the second kit component.

In a further preferred embodiment of the invention, the emulsifier of the second kit component of the kit is nonionic. Indices index m is differs from "0" and R2 and R3 can be hydrogen in formula (I). Preferably, this type of nonionic emulsifier can be selected from the group consisting of PEG-20 sorbitan monolaurate (Tween 20), PEG-4 sorbitan monolaurate (Tween 21), PEG-20 sorbitan monopalmitate (Tween 40), PEG-20 sorbitan monostearate (Tween 60), PEG-4 sorbitan monostearate (Tween 61), PEG-20 sorbitan monooleate (Tween 80), alkoxylated alkyl glyceryl ether sulfonates and a combination of two or more thereof. A particularly preferred emulsifier comprises at least PEG-20 sorbitan monolaurate (Tween 20). Yet more preferred, the emulsifier comprises PEG-20 sorbitan monolaurate (Tween 20) in the range from 60 to 100 wt. %, or from 70 to 90 wt.-%, or from 80 to 95 wt.-%, or from 90 to 99 wt.-%, each weight-% based on the total weight of the emulsifier in the second kit component.

In a further preferred embodiment of the invention, the emulsifier of the second kit component of the kit is nonionic. Indices m and n of formula (I) equal preferably both "0". This type of nonionic emulsifier is selected from the group consisting of sorbitan monolaurate (Span 20), sorbitan monopalmitate (Span 40), sorbitan monostearate (Span 60), sorbitan monooleate (Span 80), Sorbitan isostearate (Span 120) and a combination of two or more thereof. A particularly preferred emulsifier comprises at least sorbitan monolaurate (Span 20). Yet more preferred, the emulsifier comprises sorbitan monolaurate (Span 20) in the range from 60 to 100 wt. %, or from 70 to 90 wt.-%, or from 80 to 95 wt.-%, or from 90 to 99 wt.-%, each weight-% based on the total weight of the emulsifier in the second kit component.

In a further preferred embodiment of the invention, the emulsifier of the second kit component of the kit is anionic. Indices m and n of formula (I) both equal "0" for preferred anionic emulsifiers. This type of anionic emulsifiers and selected from the group consisting of Sodium dinonylnaphthalene sulfonate, Sodium 4-ethyl-1-(3-ethylpentyl)-1-octyl sulfate, Sodium dodecylbenzene sulfonate, Sodium lauryl sulfate; Sodium myristyl sulfate, Sodium dodecyl sulfate, Sodium cetyl sulfate, Sodium stearyl sulfate; Sodium cocoyl isethionate, Sodium myristoyl isethionate, and a combination of two or more thereof.

In a further preferred embodiment of the invention, the emulsifier of the second kit component of the kit is anionic. Indices m or n of formula (I) is different from "0". This type of anionic emulsifiers is selected from the group consisting of mono and dialkyl sulfosuccinates, such as Disodium lauryl sulfosuccinate; disodium laureth sulfosuccinate, Disodium stearyl sulfosuccinate, Sodium dihexyl sulfosuccinate and Sodium dioctyl sulfosuccinate, Sodium lauryl ether sulfate and a combination of two or more thereof.

In a further preferred embodiment of the invention, the emulsifier of the second kit component of the kit is cationic. Indices m, n, i and k equal "0". Preferred examples of anionic emulsifiers are Cetrimonium chloride, Cetrimonium methosulfate, and Soytrimonium chloride. Further, a combination of two or more cationic emulsifiers can be employed.

A further constituent of the second kit component is hydrogen peroxide. Hydrogen peroxide can be added as an aqueous solution, e.g. in an aqueous solution in which the amount of hydrogen peroxide is in the range of from 0.5 to 12 wt. %, with respect to the total weight of the aqueous solution.

In a preferred embodiment, the hydrogen peroxide of the second kit component is present in an amount of 2 wt.-%, 3 wt.-%, 6 wt.-%, 7.5 wt.-%, 9 wt.-%, 12 wt.-%, each wt.-% calculated as "pure" hydrogen peroxide, based on the total weight of the second kit component. For example, if the second kit component is supposed to have 6 wt. % of hydrogen peroxide, 17.14 g of an aqueous solution containing 35 wt.-% hydrogen peroxide must be employed per 100 g of second kit component.

In a further preferred embodiment of the invention, the second kit component further comprises at least one fatty alcohol. In a preferred embodiment, the second kit component of the invention comprises the at least fatty alcohol in an amount in the range from 0.1 to 10 wt.-%, or from 0.5 to 7 wt.-%, or from 0.1 to 5 wt. %, or from 1 to 5 wt.-%, each wt.-% based on the total amount of fatty alcohols per the total weight of the second kit component.

In general, any fatty alcohol can be used that is known in the art and considered appropriate by a skilled person. Preferred examples of fatty alcohols, each with from 8 to 30 carbon atoms. Examples of these further fatty alcohols are Cetyl alcohol, Stearyl alcohol and mixtures thereto of, Octyldodecanol, 2-Butyloctanol, 2-Hexyldeanol, 2-Undecylpentadecanol, Oleyl alcohol and Linoleyl alcohol (all according to INCI nomenclature). The second kit component can comprise at least one, or a combination of two or more fatty alcohols, in particular from the ones mentioned in the list of suited example fatty alcohols above.

A further preferred embodiment of the invention is a kit, wherein the kit is characterized by at least one, preferably two or more, yet more preferred all of these features:
(A) A total amount of the organic phosphate ester compounds of the first kit component is in the range from 0.1 to 10 wt.-%, based on total weight of the first component;
(B) A total amount of the amino acid of the first kit component is in the range from 0.5 to 20 wt.-%, based on total weight of the first component;
(C) A total amount of the alkaline agent of the first kit component is in the range from 1 to 15 wt.-%, based on total weight of the first component;
(D) A total amount of one or more oxidation dyes of the first kit component is in the range from 0 to 10 wt.-%, based on total weight of the first component;
(E) A total amount of the hydrogen peroxide of the second kit component is in the range from 0.5 to 12 wt.-%, based on total weight of the second component;
(F) A total amount of the fatty alcohol of the second kit component is in the range from 0.1 to 10 wt.-%, based on total weight of the second component;
(G) A total amount of the emulsifier of the second kit component is in the range from 0.1 to 10 wt.-%, based on total weight of the second component;
or a combination of two or more of (A), (B), (C), (D), (E), (F) and (G).

A further preferred embodiment of the invention is a kit, wherein the kit, yet more preferred the second kit component, is characterized by a combination of at least the following feature of the above list: (E), (E) (F), (E) (G), (E) (F) (G), each of the above mentioned features.

A yet further preferred embodiment of the invention is a kit, wherein the kit is characterized by a combination of at least the following feature of the above list: (A) (E), (A) (E) (F), (A) (E) (G), (A) (E) (F) (G), each of the above mentioned features.

A further preferred embodiment of the invention is a kit, wherein the kit is characterized by at least one of these features:
(a) the first kit component has a pH in the range from 7.0 to 12, preferably 9.0 to 10.5;
(b) the second kit component has a pH in the range from 2.0 to 4.0; pref. 2.5 to 3.0; and
(c) wherein a weight ratio of the first kit component to the second kit component in the kit is in the range from 2:1 to 1:3.

In a preferred embodiment of the invention is a kit, wherein the kit is characterized by a combination of at least the following feature of the above list: (a)(b), (a)(c), (b)(c), (a)(b)(c).

A second aspect of the invention is a process of manufacturing a composition, wherein the composition is the second kit component as described by the first aspect of the invention or any one of its embodiments, wherein the process comprises at least these steps:
i) Providing the at least one fatty alcohol, and an amount of water;
ii) Mixing the at least one fatty alcohol and the amount of water to form an emulsion precursor;
iii) Providing and adding to the emulsion precursor an amount of hydrogen peroxide and the at least one emulsifier to form a pre-emulsion;
iv) Adjusting the pH of the pre-emulsion to a value in the range from 1.5 to 4.

In a further embodiment, the emulsion precursor can be prepared in presence of a Polyethylenglycol-monoalkylether or a further emulsifier, as defined in the present invention. In case Polyethylenglycol-monoalkylether is also added during preparation of the emulsion precursor, an aqueous solution of the at least one emulsifier in step iii) is added preferentially after the addition of hydrogen peroxide.

The pH can be adjusted by adding, under stirring, amounts of acids of bases, preferably inorganic acids, such as Phosphoric acids and inorganic bases, such as sodium hydroxide. A pH meter is used to track the pH of the emulsion. Stirring can be done by using a mechanical stirrer, or by other means, such as, for example, bubbling a non-reactive gas, such as air or nitrogen, through the emulsion.

The second kit component is obtained by completing step iv). Further constituents can be added to the second kit component which are not explicitly cited by step i) to iv) above.

Details and embodiments of the second kit component of the first aspect of the invention, in particular those embodiments referring to preferred constituents and/or combinations, are also details and embodiments to the second aspect of the invention. Some of these constituents are preferably added prior to mixing in step ii) and/or some are preferably added afterwards.

The composition of the invention according to the second aspect can be prepared according to different procedures. According to a conventional protocol, the composition of the invention is produced in a batch process. Since the viscosity of the composition of the invention is rather low (i.e. in the range of from 1 to 40 Pa·s), the composition is well suited for being manufactured in a continuous process. Accordingly, an embodiment of the process of the invention is performed as a continuous process. In both processes, continuous or batch, a dye-free composition is prepared in a first step. A particular advantage of this composition of the invention is its versatility. For example, optional further constituents can be added at any stage of the process. Control of heat generation is advantageous because the viscosity of mixtures in the production process often varies with temperature. Such conditions are prerequisites for using a static mixer or a dynamic mixer, if the composition of the second aspect of the invention should be adopted to a specific shade employing the principle of delayed differentiation. Preferably, double-chamber pumps are employed with which the constant pressure and output can be adjusted to the viscosity of the fluid. Preferably the pressure can be selected in the range of from 1 to 200 bar. Manufacturing the composition of the invention using a continuous process eliminates time consuming batch production, especially the time consuming cleaning cycles. Furthermore, different shades can be produced within short delays because a static mixer has low mixing volume and in this case no extensive cleaning of mixing apparatus is necessary. This is of considerable economic advantage.

A third aspect of the invention is a composition obtainable by a process according to the second aspect of the invention and embodiments thereto.

A fourth aspect of the invention is a composition, which preferably is designed to be used in an at least two component kit for coloring keratin fibers, in particular those of humans, wherein the composition of the second component comprises at least these constituents:
B-a) at least one emulsifier;
B-b) hydrogen peroxide;
B-c) at least one fatty alcohol;
B-d) water;
wherein the at least one emulsifier is described by formula (I),

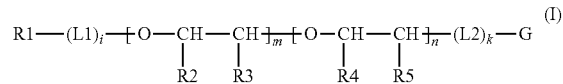

wherein
R1 represents a saturated or unsaturated, linear or branched C7-C24 chain;
L1 is a linking group and represents a carbonyl or a sulfonyl group;
R2, R3, R4, R5 represent each individually a hydrogen atom or a methyl group,
wherein at least one of R2 or R3 is a hydrogen atom, and
wherein at least one of R4 or R5 is a hydrogen atom;
L2 is a linking group independent from L1 and is selected from the group consisting of a carbonyl group, a carboxylic ester group, a sulfonyl group, a sulfonic ester group, a phenylene group, or a —OCH$_2$—CH(OH)—CH$_2$— group;
i, k, are independent from each other and can have an integer value of 0 or 1;
m and n are each independent from each other and can have an integer value of at least 0; and
G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

Details and embodiments of the second kit component of the first aspect of the invention, in particular those embodiments referring to preferred constituents and/or combinations, are also details and embodiments to the fourth aspect of the invention.

A fifth aspect of the invention is a kit which is preferably designed for coloring keratin fibers, in particular those of humans or pet animals, wherein the kit comprises in spatially separated form at least a first and second kit component, wherein the second kit component comprises a composition as described for the composition according third and/or fourth aspect of the invention. Details and embodiments of the second kit component of the first aspect of the invention, in particular those embodiments referring to preferred constituents and/or combinations, are also details and embodiments to the fifth aspect of the invention.

A sixth aspect of the invention is a ready-to-use composition obtainable by mixing the kit components of the kit according the first aspect of the invention or one or more embodiments thereto, or according to the fifth aspect of the invention or one or more embodiments thereto.

As described before, hair coloring composition are usually manufactured and provided as two component kits, wherein a first kit component has a basic pH and comprises the primary intermediates and the color coupling agents. The second kit component comprises a hydrogen peroxide composition which is usually stabilized by an amount of acid. According to the present invention, the second kit component also comprises at least one emulsifier. Both kit components are often provided in cream- or gel-like form.

Prior to use, a ready-to-use composition is produced by mixing the first and the second kit component either by stirring in a bowl or by shaking in a container, e.g. a bottle or a jar. The ready-to-use mixture is then applied to the hair using a brush or an applicator tool. Preferably, coloring mixtures have a certain, higher viscosity in order to prevent dripping during the treatment of the hair. Optimum results in the oxidative coloring of hair are usually achieved by ready-to-use mixtures which are adjusted to a pH in the range of from 9.0 to 10.5. Usually, the first, second and optionally further kit components are mixed directly prior to application to the hair in a ratio of from 2:1 to 1:3. Ideally, mixing is performed immediately prior to application to the hair so that formation of the oxidative dyes (the color) does not occur before the mixture is applied to the hair.

After working the ready-to-use composition for a few minutes (to insure uniform application to all of the hair), the ready-to-use composition is allowed to remain on the hair for an amount of time sufficient for obtaining the target shade. The remaining period is in the range of from 5 to 90 minutes, preferably 10 to 60 minutes, and usually about 30 minutes.

In the kit composition of the invention, a third kit component may be present. In this event, the first, second and third kit component can be mixed either immediately before use and applied together. Preferably this procedure is carried out if, for instance, the third kit composition comprises a dye which does not support conditions present in the first kit component (e.g. reducing conditions). Alternatively, the content of the third kit composition is applied after an optional rinse step immediately after processing as a post-treatment; in such cases the third kit composition can comprise a conditioner.

A seventh aspect of the invention is a process of preparing a ready-to-use composition wherein the process comprises at least these steps:
(i) Providing a kit according to the first aspect of the invention or one or more of its embodiments or according to the third aspect of the invention or one or more of its embodiments,
(ii) Mixing the kit components.

Thereby the ready-to-use composition of the seventh aspect of the invention is obtained.

In an embodiment of the invention, mixing the kit components, more specifically mixing the first and the second kit component is performed in a bottle. Preferably, an applicator bottle is used, as familiar to hair stylists and/or home users of hair coloring kit users.

In an embodiment of the invention, mixing the kit components, more specifically mixing the first and the second kit component is performed in a bowl. A mixing tool or a hair color application tool is used for mixing the components. An example of such a mixing tool or hair color application tools is a brush.

An eighth aspect of the invention is a ready-to-use composition according to the sixth aspect of the invention or at least one of the embodiments thereto, or a ready-to-use composition obtainable by a process according to the seventh aspect of the invention. Particularly preferred is the ratio of the first kit component and the second kit component in the range of from 2:1 to 1:3, each number based on parts by weight with respect to the total amount of the ready-to-use composition.

A ninth aspect of the invention is a process for coloring keratin fibers, comprising the steps of:
I. providing keratin fibers;
II. contacting the keratin fibers of step I. with a ready-to-use composition according to the sixth aspect of the invention or one or more of the embodiments thereto, or with a ready-to-use composition obtainable by a process according to the seventh aspect of the invention or one or more of the embodiments thereto;
III. optionally rinsing the keratin fibers, preferably with water;
IV. optionally drying the keratin fibers, preferably using a towel or using a flow of air.

Numerous kinds of keratin fibers are known to those skilled in the art. Preferred keratin fibers in the context of the present invention are human hair and animal hair. The process for coloring keratin fibers is described in the following with regard to human hair. This is not intended to limit the scope of the claimed process. To the contrary, it is understood that the process can be applied in the same way to any other kind of keratinous material.

Oxidative hair coloring compositions like those according to the present invention are usually sold in kits comprising, in spatially separated and thus, individually packaged form kit components such as separate containers, a first kit component containing the dye component comprising the oxidative dye, precursors and a base and; a second kit container containing a developer composition comprising the oxidizing agent (usually hydrogen peroxide), and in the present invention at least one emulsifier and at least one fatty acid. For example and as mentioned above, the first and the second kit component can be presented in two containers. The consumer then dispenses the first and the second kit component in a mixing reservoir, e.g. a bowl, immediately before use and mixes the first and the second kit component thereby obtaining a ready-to-use composition. The ready-to-use composition is then applied onto the hair.

After processing the ready-to-use composition (to insure uniform application to all of the hair), the ready-to-use composition is often allowed to remain on the hair for an amount of time sufficient for the dyeing to take place. The remaining period is in the range of from 5 to 90 minutes, preferably 10 to 60 minutes, and usually about 30 minutes. The consumer then rinses his/her hair thoroughly with tap water and allows it to dry. It is observed that the hair has changed from its original color to the desired color.

When present in the composition of the invention, the optional hair care agent can be provided as a third kit component, e.g. in a third container. In this case, the first, second an the third kit component can be mixed immediately before use and applied together, or the third kit component can be applied (after an optional rinse step) as a post-treatment immediately after the ready-to-use composition resulting from the mixture of the other containers.

In a preferred embodiment of the ninth aspect of the invention, the first kit component and the second kit component are provided in a weight ratio of the first kit component and the second kit component in the range from 2:1 to 1:3, each number based on parts by weight.

A tenth aspect of the invention is a use of an emulsifier in combination with at least one organic phosphate ester compound to reduce the viscosity of a hair coloring composition, wherein the at least one emulsifier is described by formula (1),

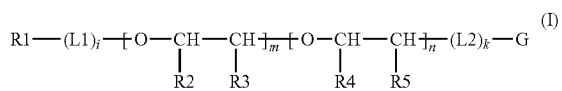

wherein
R1 represents a saturated or unsaturated, linear or branched C7-C24 chain;
L1 is a linking group and represents a carbonyl or a sulfonyl group;
R2, R3, R4, R5 represent each individually a hydrogen atom or a methyl group,
  wherein at least one of R2 or R3 is a hydrogen atom, and
  wherein at least one of R4 or R5 is a hydrogen atom;
L2 is a linking group independent from L1 and is selected from the group consisting of a carbonyl group, a carboxylic ester group, a sulfonyl group, a sulfonic ester group, a phenylene group or a —OCH$_2$—CH(OH)—CH$_2$— group;
i, k, are independent from each other and can have an integer value of 0 or 1;
m and n are each independent from each other and can have an integer value of at least 0;
  wherein the sum of m and n is different from 0; and
  wherein the sum of m and n is different from 0;
G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

Details and embodiments of the second kit component of the first aspect of the invention, in particular those embodiments referring to preferred constituents and/or combinations, are also details and embodiments to the fourth aspect of the invention.

FIGURES

FIG. 1 exhibits a process of manufacturing a composition useful as second kit component in a kit for coloring keratin fibers, like human or animal hair.
FIG. 2 shows a kit for coloring keratin fibers consisting of 1 tube and 1 applicator bottle.
FIG. 3 exhibits a process for preparing a ready-to-use composition.
FIG. 4 shows a process for coloring keratin fibers.
FIG. 5 is a schematic of model head.

EXAMPLES

Figure 1:
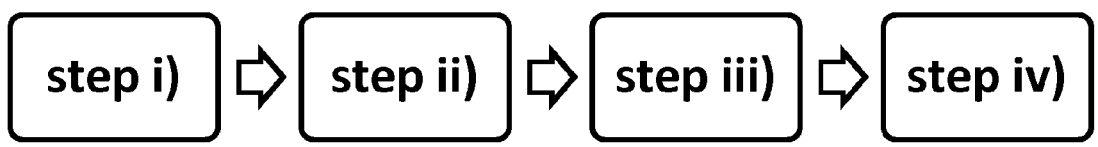
FIG. 1 shows a process of manufacturing a composition, which can be employed as second kit component in an at least two component kit. The process comprises these steps: i) providing at least one fatty alcohol and an amount of water as constituents; ii) mixing the constituents provided in step i), for example by using a heated mixer. In this step, heat can be applied to the mixture to achieve a temperature of 85° C. and maintain this temperature for at least 10 minutes whereby an emulsion precursor is obtained; afterwards, the emulsion precursor can be cooled to 50° C.; iii) adding an amount of 30 wt.-% aqueous solution of hydrogen peroxide to the emulsion precursor and an emulsifier as defined by formula (I) I claim 1 under constant stirring; wherein a pre-emulsion is formed; and iv) then adjusting the pH of the pre-emulsion to a value in the range of from 1.5 to 4, by adding an amount of inorganic acid under continued stirring, e.g. phosphoric acid. At this stage, the composition used as second kit component is obtained.
Figure 2:
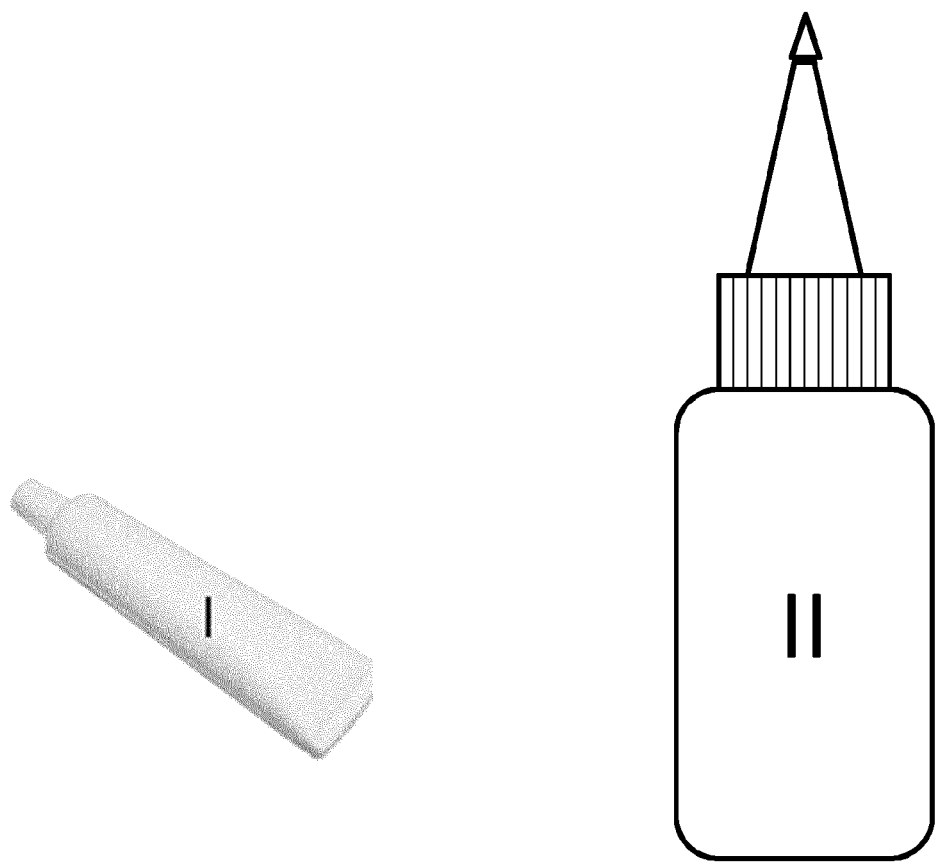
FIG. 2 shows a kit for coloring keratin fibers consisting of 2 tubes with cream wherein tube I comprises a first kit component and tube II comprises a second kit component. The second kit component can be a composition as manufactured according to FIG. 1.
Figure 3:
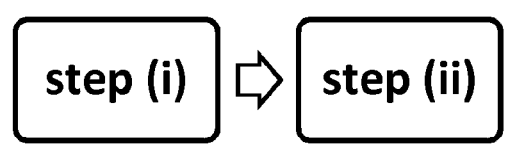
FIG. 3 exhibits a process for preparing a ready-to-use composition. The process comprises at least two steps. In step (i), a kit as in FIG. 2 is provided. The two tubes I and II are opened and the first and second kit component is dispensed into a vessel, e.g. a bowl. Then, the first and second kit components are mixed in step (ii) which results in a ready-to-use composition.
Figure 4:
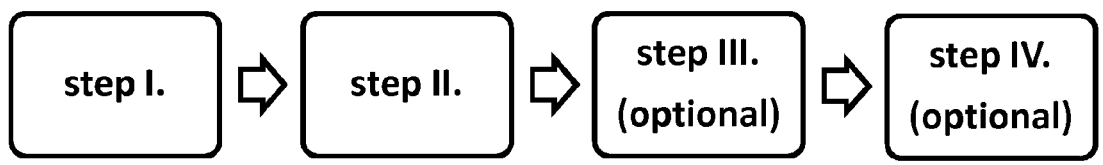
FIG. 4 shows a process for coloring keratin fibers, comprising these steps: I. providing keratin fibers; II. contacting the keratin fibers of step I. with a ready-to-use composition which was obtained by mixing the components of a kit as in FIG. 2, further allowing the ready-to-use composition to remain on the keratin fibers for a period of time; III. (optionally) rinsing the keratin fibers; IV. (optionally) drying the keratin fibers.
Figure 5:
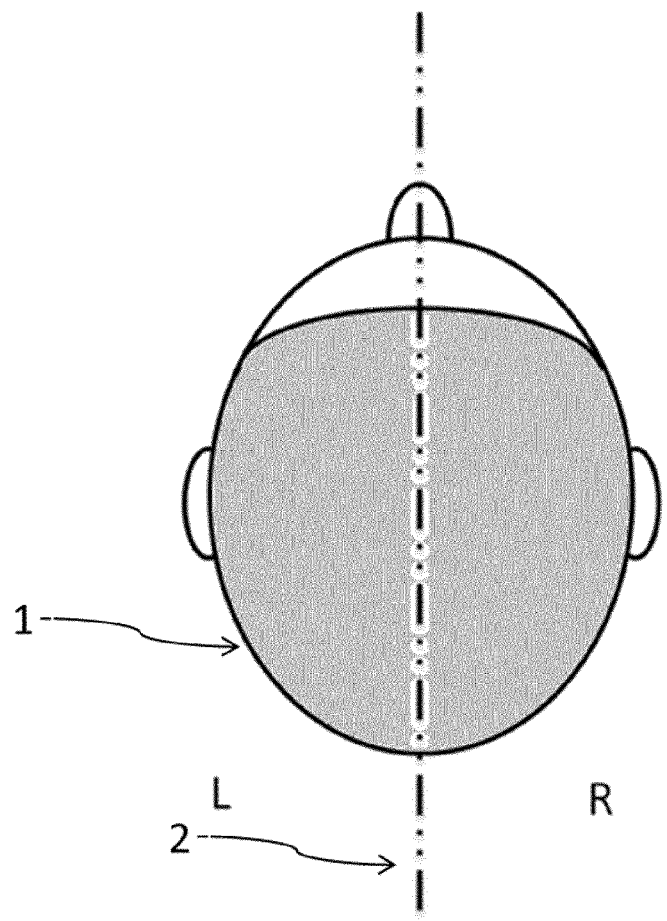
FIG. 5 is a schematic of model head 1. The left side L of the head with hair (not shown here) was treated with a reference coloring composition, the right side R of the head with hair (not shown here) was treated with a composition obtained from mixing the two component kit under evaluation.

The following examples illustrate some aspects of the invention. It is understood that the examples and embodiments described herein are for illustrative purposes only and that various modifications or changes in light thereof may be suggested by one skilled in the art without departing from the scope of the present invention. Accordingly, the invention is not limited by or to the examples.

Amounts mentioned in the tables below refer to wt.-% if not indicated to the contrary. When referring to rinsing or washing of hair with water in the examples, this is tap water, with a hardness of dH=8.4 (equals 1.5 mmol $CaCO_3$/liter $H_2O$). When referring to water as component of a composition (in tables, denoted as "aqua"), this is demineralized water as used for cosmetic purposes.

The viscosity of an example was measured with a RHEO-MAT R180 from ProRHEO GmbH, D-75382 Althengstett, Germany. The parameters used for the determination of the viscosity are summarized in Table A

TABLE A

Parameters in determining viscosities of color cream, developer and ready-to-use mixtures

|  | Color cream | Developer | Ready-to-use mixture |
|---|---|---|---|
| Temperature | 25° C. | 25° C. | 25° C. |
| Spindle # | 3 | 2 | 3 |
| Rotational speed | 5 rpm | 100 rpm | 5 rpm |

Example 1: Developer Compositions

TABLE 1

Developer compositions, comparative and according to the invention

| Ingredients | Example 1a (comparative) | Example 1b (according to the invention) |
|---|---|---|
| Hydrogen peroxide 35% | 17.100 | 17.100 |
| Cetearyl alcohol (50:50)* | 5.000 | 5.000 |
| Cremophor A25 | 2.500 | 2.500 |
| Tween 20 | —/— | 2.500 |
| Paraffinum liquidum | 0.600 | 0.600 |
| Merquat 295 | 0.500 | 0.500 |
| Disodium hydrogen phosphate | 0.050 | 0.050 |
| Phosphoric acid 85% | 0.050 | 0.050 |
| Etidronic acid | 0.025 | 0.025 |
| Water ad | 100.000 | 100.000 |

*Cetearyl alcohol 50:50 is a 1:1 mixture of Cetyl alcohol and Stearyl alcohol, based on their weights.

The pH of the developer compositions was adjusted to 2.5 by addition of diluted Phosphoric acid and Sodium hydroxide, respectively, to the composition as described in Table 1. The viscosity of the examples 1a-1b was 3'000 mPas.

Example 2: Hair Color Creams

TABLE 2

Color cream compositions based on Dicetyl Phosphate and Ceteth-10 Phosphate (both color creams are not inventive)

| Ingredients | Example 2a: black | Example 2b: light blond |
|---|---|---|
| Crodafos CES*) | 8.00% | 10.00% |
| Xanthan gum | 0.10% | 0.30% |
| Propylene glycol | 3.00% | 5.00% |
| Glycine | 5.00% | 12.00% |
| Arginine | 1.00% | — |
| Sodium hydroxide | 4.90% | 6.80% |
| Ascorbic acid | 0.30% | 0.30% |
| Sodium sulfite | 0.30% | 0.30% |
| EDTA | 0.20% | 0.20% |
| p-Toluenediamine sulfate | 4.00% | 0.04% |
| Resorcinol | 1.00% | 0.015% |
| m-Aminophenol | 0.70% | 0.002% |
| 2,4-Diaminophenoxy ethanol sulfate | 0.60% | 0.010% |
| Tris(hydroxymethyl)aminomethane | 3.00% | 5.00% |
| Water, ad | 100% | 100% |

Crodafos CES*): blend of Cetearyl Alcohol, Dicetyl Phosphate and Ceteth-10 Phosphate.

The viscosity of composition 2a is 240'000 mPas, and the viscosity of 2b is 235'000 mPas. Both compositions are ammonia-free.

Example 3: Comparative Trials—Brush-and-Bowl Application

The hair color creams of example 2 and the developer compositions of example 1 were mixed thoroughly in a bowl by means of a brush at a 1:1.5 ratio (50 g color cream and 75 g developer) and viscosities were measured.

TABLE 3.1

Viscosities of ready-to-use mixtures, ratio 1:1.5

|  | Comparative developer 6% Example 1a | Inventive developer 6% Example 1b |
|---|---|---|
| Hair color cream of Example 2a | Viscosity = 72'700 mPas | Viscosity = 39'000 mPas |
| Hair color cream of Example 2b | Viscosity = 80'700 mPas | Viscosity = 38'500 mPas |
| Color result | Equal in both cases for both shades | |

The viscosity of the mixture obtained from the inventive developer composition 1b in a 1:1.5 ratio is approximately half of the mixture obtained from a standard developer composition 1a.

In another experiment the hair color creams of example 2 and the developer compositions of example 1 were mixed thoroughly in a bowl by means of a brush at a 1:2 ratio (40 g color in cream and 80 g developer) and viscosities were measured.

TABLE 3.2

Viscosities of ready-to-use mixtures, ratio 1:2

|  | Comparative developer 6% Example 1a | Inventive developer 6% Example 1b |
|---|---|---|
| Hair color cream of Example 2a | Viscosity = 69'800 mPas | Viscosity = 26'400 mPas |
| Hair color cream of Example 2b | Viscosity = 77'700 mPas | Viscosity = 26'100 mPas |
| Color result | Equal in both cases for both shades | |

The viscosity of the mixture obtained from the inventive developer composition 1b in a 1:2 ratio is approximately a third of the mixture obtained from a standard developer composition 1a.

Example 4: Comparative Trials—Bottle Application

Wella Illumina 7/medium blond. According to the INCI declaration, the color cream comprises Dicetyl Phosphate and Ceteth-10 Phosphate. This color cream was mixed with a) a commercial developer labelled Welloxon 6% and b. the inventive developer according to Example 1b.

The recommended developer for Illumina is Welloxon 6% and consists of Water, Hydrogen Peroxide, Cetearyl Alcohol, Ceteareth-25, Salicylic Acid, Phosphoric Acid, Disodium Phosphate and Etidronic Acid (INCI declaration).

TABLE 4

| Test hair color cream | Commercial developer | Inventive developer |
| --- | --- | --- |
| Wella Illumina 7/ | Welloxon Perfect 6%, developer from Wella | Example 1b, 6% |
| Mixing ratio Illumina:Developer | 1:1 | 1:1 |
| Mixability in an applicator bottle and visual inspection of result | Mixing is very difficult, despite intense shaking for 30 seconds inhomogeneous regions are clearly visually detectable in the composition. | Mixing is very easy. A visually homogeneous mixture was obtained after shaking for 10 seconds. |
| Discharging. | Due to the high viscosity, discharging of the inhomogeneous composition requires forceful squeezing of the bottle; a large amount of content remains in the bottle (approx. one third of the ready to use composition). | Easy discharging. Only 10%- to 15% of the mixture remains in the applicator bottle. |
| Application with bottle to hair judged by the same individual | Difficult | Easy |
| Color result | Almost equal | |

The viscosity of the ready-to-use mixture obtained from Wella Illumina 7/and Welloxon Perfect 6% is relatively high and therefore useful for brush-and-bowl application only, whereas the viscosity obtained from Wella Illumina 7/together with the inventive developer 6% of Example 1b is considerably lower and therefore very useful for bottle application. Even though the mixture obtained with the inventive developer composition is less viscous, it remained drip-free.

Example 5: Comparative Test of Developers Comprising Emulsifiers of Formula (I) without PEG Increment Vs. Analogous Emulsifiers with PEG Increment All emulsifier amounts were set to 1.5% by weight.

TABLE 5

Developer compositions according to the invention

| Ingredients | Example 5a | Example 5b | Example 5c | Example 5d |
| --- | --- | --- | --- | --- |
| Hydrogen peroxide 35% | 17.100 | 17.100 | 17.100 | 17.100 |
| Cetearyl alcohol (50:50) | 5.000 | 5.000 | 5.000 | 5.000 |
| Cremophor A25 | 2.500 | —/— | —/— | —/— |
| Tween 20 | 1.500 | —/— | —/— | —/— |
| Span 20 | —/— | 1.500 | —/— | —/— |
| Sodium lauryl sulfate | —/— | —/— | 1.500 | —/— |
| Sodium laurylether sulfate, 28% aq. solution*) | —/— | —/— | —/— | 1.500 |
| Paraffinum liquidum | 0.600 | 0.600 | 0.600 | 0.600 |
| Merquat 295 | 0.500 | 0.500 | 0.500 | 0.500 |
| Disodium hydrogen phosphate | 0.050 | 0.050 | 0.050 | 0.050 |
| Phosphoric acid 85% | 0.050 | 0.050 | 0.050 | 0.050 |
| Etidronic acid | 0.025 | 0.025 | 0.025 | 0.025 |
| Water ad | 100.000 | 100.000 | 100.000 | 100.000 |

*): added were 5.36% of Sodium laurylether sulfate, 28% in water, to get 1.5%

The pH of the developer compositions 5a-5d was adjusted to 2.5 by the addition of diluted Phosphoric acid and Sodium hydroxide, respectively.

The developer compositions of examples 5a-d were used for mixing with the color cream of example 2b in an applicator bottle; the cream-developer ratio was 1:1.5. Shaking for 30 seconds give the results shown in Table 5.2.

TABLE 5.2

Usability of developer compositions 5a-d for bottle application

| | Emulsifier without PEG increment | Emulsifier with PEG increment |
| --- | --- | --- |
| Emulsifier (example) Viscosity-reducing effect | Sodium lauryl sulfate (5c) no | Sodium laurylether sulfate (5d) yes |
| Emulsifier Viscosity-reducing effect | Span 20 (5b) no | Tween 20 (5a) yes |

With the developer compositions comprising the emulsifiers without the PEG increment it was not possible to obtain a ready-to-use composition useful for bottle application as the mixture was too viscous and some areas remained unmixed, whereas the developer compositions comprising the emulsifiers with the PEG increment were able to reduce the viscosity of the mixture and bottle application was possible.

The following table 6 cites commercial source for some of the compounds:

TABLE 6 supplier information for selected compounds

| | |
|---|---|
| Cremophor A25 | BASF, Ludwigshafen, Germany |
| Paraffinum liquidum | Specialties Exxonmobil, Germany |
| Merquat 295 | Lubrizol Ltd, Belper, Derby, DE56 1QN, England |
| Crodafos CES | Croda International Plc, Snaith, United Kingdom |
| Tween 20 | Croda International Plc, Snaith, United Kingdom |
| Span 20 | Croda International Plc, Snaith, United Kingdom |
| Wella Illumina 7/and Welloxon 6% | Wella (Coty), Darmstadt, Germany |

The invention claimed is:

1. A kit, comprising in spatially separated form at least two kit components:
   A) a first kit component comprising at least these constituents:
      A-a) at least one alkaline agent;
      A-b) at least one amino acid;
      A-c) at least one organic phosphate ester compound selected from the group consisting of a monoester of a phosphate of one or more alkoxylated fatty alcohols, a diester of a phosphate of one or more non-alkoxylated fatty alcohols, and a mixture of both;
      A-d) water;
   B) a second kit component comprising at least these constituents:
      B-a) at least one emulsifier;
      B-b) hydrogen peroxide;
      B-c) at least one fatty alcohol;
      B-d) water;
   wherein the emulsifier is described by formula (I),

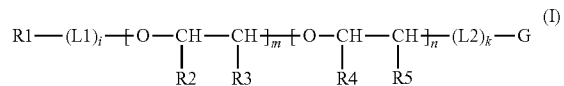

wherein
R1 represents a saturated or unsaturated, linear or branched C7-C24 chain;
L1 is a linking group and represents a carbonyl or a sulfonyl group;
R2, R3, R4, R5 represent each individually a hydrogen atom or a methyl group,
   wherein at least one of R2 or R3 is a hydrogen atom, and
   wherein at least one of R4 or R5 is a hydrogen atom;
L2 is a linking group independent from L1 and is selected from the group consisting of a carbonyl group, a carboxylic ester group, a sulfonyl group, a sulfonic ester group, a phenylene group, or a —OCH$_2$—CH(OH)—CH$_2$— group;
i, k, are independent from each other and can have an integer value of 0 or 1;
m and n are each independent from each other and can have an integer value of at least 0;
G is selected from the group consisting of sorbitan; a sorbitan where the hydroxy groups are partially or fully substituted by polyethyleneoxy chains; an anionic group selected from the group consisting of a sulfonic acid group, a sulfate group, a C1-alkylenesulfonic acid group, and a C2-alkylenesulfonic acid group; a cationic group which includes a quarternized ammonium cation and a combination of two or more thereof.

2. The kit according to claim 1, wherein the organic phosphate ester compound in the first kit component comprises at least Dicetyl Phosphate and Ceteth-10 Phosphate.

3. The kit according to claim 1, wherein the emulsifier of the second kit component is nonionic and selected from the group consisting of PEG-20 sorbitan monolaurate (Tween 20), PEG-4 sorbitan monolaurate (Tween 21), PEG-20 sorbitan monopalmitate (Tween 40), PEG-20 sorbitan monostearate (Tween 60), PEG-4 sorbitan monostearate (Tween 61), PEG-20 sorbitan monooleate (Tween 80), alkoxylated alkyl glyceryl ether sulfonates and a combination of two or more thereof.

4. The kit according to claim 1, wherein the emulsifier of the second kit component is nonionic and selected from the group consisting of sorbitan monolaurate (Span 20), sorbitan monopalmitate (Span 40), sorbitan monostearate (Span 60), sorbitan monooleate (Span 80), Sorbitan isostearate (Span 120) and a combination of two or more thereof.

5. The kit according to claim 1, wherein the emulsifier of the second kit component is anionic and selected from the group consisting of Sodium dinonylnaphthalene sulfonate, Sodium 4-ethyl-1-(3-ethylpentyl)-1-octyl sulfate, Sodium dodecylbenzene sulfonate, Sodium lauryl sulfate; Sodium myristyl sulfate, Sodium dodecyl sulfate, Sodium cetyl sulfate, Sodium stearyl sulfate; Sodium cocoyl isethionate, Sodium myristoyl isethionate; mono and dialkyl sulfosuccinates; disodium laureth sulfosuccinate, Disodium stearyl sulfosuccinate, Sodium dihexyl sulfosuccinate and Sodium dioctyl sulfosuccinate, and a combination of two or more thereof.

6. The kit according to claim 1, wherein the emulsifier of the second kit component is cationic and selected from the group consisting of Cetrimonium chloride, Cetrimonium methosulfate, and Soytrimonium chloride.

7. The kit according to claim 1, wherein the second kit component comprises in the range from 0.1 to 10 weight-% of the emulsifier, based on the total weight of the second kit component.

8. The kit according to claim 1, wherein the first kit component optionally further comprises one or more oxidation dyes, and wherein the kit is characterized by at least one of these features:
   (A) A total amount of the organic phosphate ester compounds of the first kit component is in the range from 0.1 to 10 wt.-%, based on total weight of the first component;
   (B) A total amount of the amino acid of the first kit component is in the range from 0.5 to 20 wt.-%, based on total weight of the first component;
   (C) A total amount of the alkaline agent of the first kit component is in the range from 1 to 15 wt.-%, based on total weight of the first component;
   (D) A total amount of one or more oxidation dyes of the first kit component is in the range from 0 to 10 wt.-%, based on total weight of the first component;
   (E) A total amount of the hydrogen peroxide of the second kit component is in the range from 0.5 to 12 wt.-%, based on total weight of the second component;
   (F) A total amount of the fatty alcohol of the second kit component is in the range from 0.1 to 10 wt.-%, based on total weight of the second component;
   (G) A total amount of the emulsifier of the second kit component is in the range from 0.1 to 10 wt.-%, based on total weight of the second component;
   or a combination of two or more of (A), (B), (C), (D), (E), (F) and (G).

9. The kit according to claim 1, wherein the kit is characterized by at least one of these features:
   (a) the first kit component has a pH in the range from 7.0 to 12;

(b) the second kit component has a pH in the range from 2.0 to 4.0;
(c) wherein the weight ratio of the first kit component to the second kit component in the kit is in the range from 2:1 to 1:3.

10. The kit according to claim 1, wherein the amino acid of the first kit component is selected from the group consisting of glycine, serine, asparagine, threonine, glutamine, arginine, lysine, α- or β-alanine, and a combination of two or more thereof.

11. The kit according to claim 1, wherein the alkaline agent of the first kit component is selected from the group consisting of ammonium hydroxide, an alkanolamine, diethanolamine, triethanolamine, monopropanolamine, dipropanolamine, tripropanolamine, 2-amino-2-methyl-1,3-propanediol (AMPD), 2-amino-2-ethyl-1,3-propanediol (AEPD), 2-amino-2-methyl-1-propanol (AMP), 2-amino-2-hydroxymethyl-1,3-propanediol (TRIS), sodium and potassium hydroxide, ammonium carbonate, ammonium bicarbonate, ammonium carbamate, and a combination of two or more thereof.

12. The kit according to claim 1, wherein the first kit component further comprises at least one oxidative dye, and wherein the at least one oxidative dye is selected from the group of p-Phenylenediamines, p-Aminophenols, 4,5-Diaminopyrazoles, Pyrimidines, Resorcinols, m-Phenylenediamines, o-Aminophenols, m-Aminophenols, 1-Naphthols, Pyridines, Indoles, Indolines, and a combination of two or more thereof.

13. The kit according to claim 1, wherein the at least one fatty alcohol of the second kit component comprises from 8 to 30 carbon atoms.

14. A process of manufacturing a composition, wherein the composition is the second kit component in claim 1, wherein the process comprises at least these steps:
    i) Providing the at least one fatty alcohol, and an amount of water;
    ii) Mixing the at least one fatty alcohol and the amount of water to form an emulsion precursor;
    iii) Providing and adding to the emulsion precursor an amount of hydrogen peroxide and the at least one emulsifier to form a pre-emulsion;
    iv) Adjusting the pH of the pre-emulsion to a value in the range from 2 to 4.

15. A composition obtainable by a process according to claim 14.

16. A kit comprising in spatially separated form at least a first and second kit component, wherein the second kit component comprises a composition as claimed according to claim 15.

17. A ready-to-use composition obtainable by mixing the kit components of the kit according to claim 1.

18. A process of preparing a ready-to-use composition wherein the process comprises at least these steps:
    (i) Providing a kit according to claim 1,
    (ii) Mixing the kit components.

19. The process of claim 18, wherein at least the mixing is performed in a bottle.

20. The process of claim 18, wherein at least the mixing is performed a bowl, wherein a mixing tool or a hair color application tool is used.

21. The ready-to-use composition according to claim 17, wherein the ratio of the first kit component and the second kit component is in the range of from 2:1 to 1:3, each number based on parts by weight.

22. A process for coloring keratin fibers, comprising the steps of:
    I. providing keratin fibers;
    II. contacting the keratin fibers of step I. with a ready-to-use composition according to claim 17.

23. The process of claim 22, wherein the first kit component and the second kit component are provided in a weight ratio of the first kit component and the second kit component in the range from 2:1 to 1:3, each number based on parts by weight.

* * * * *